United States Patent

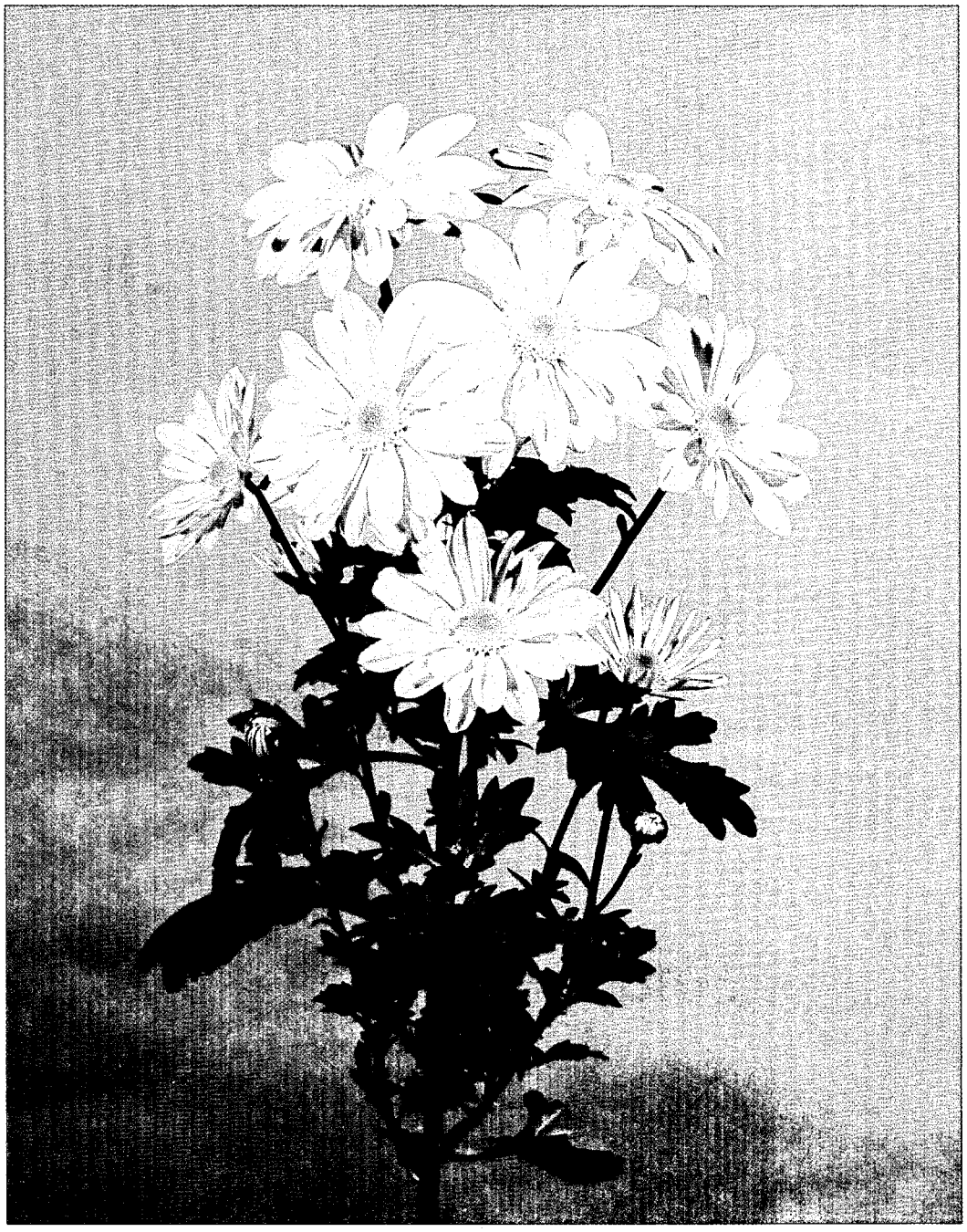

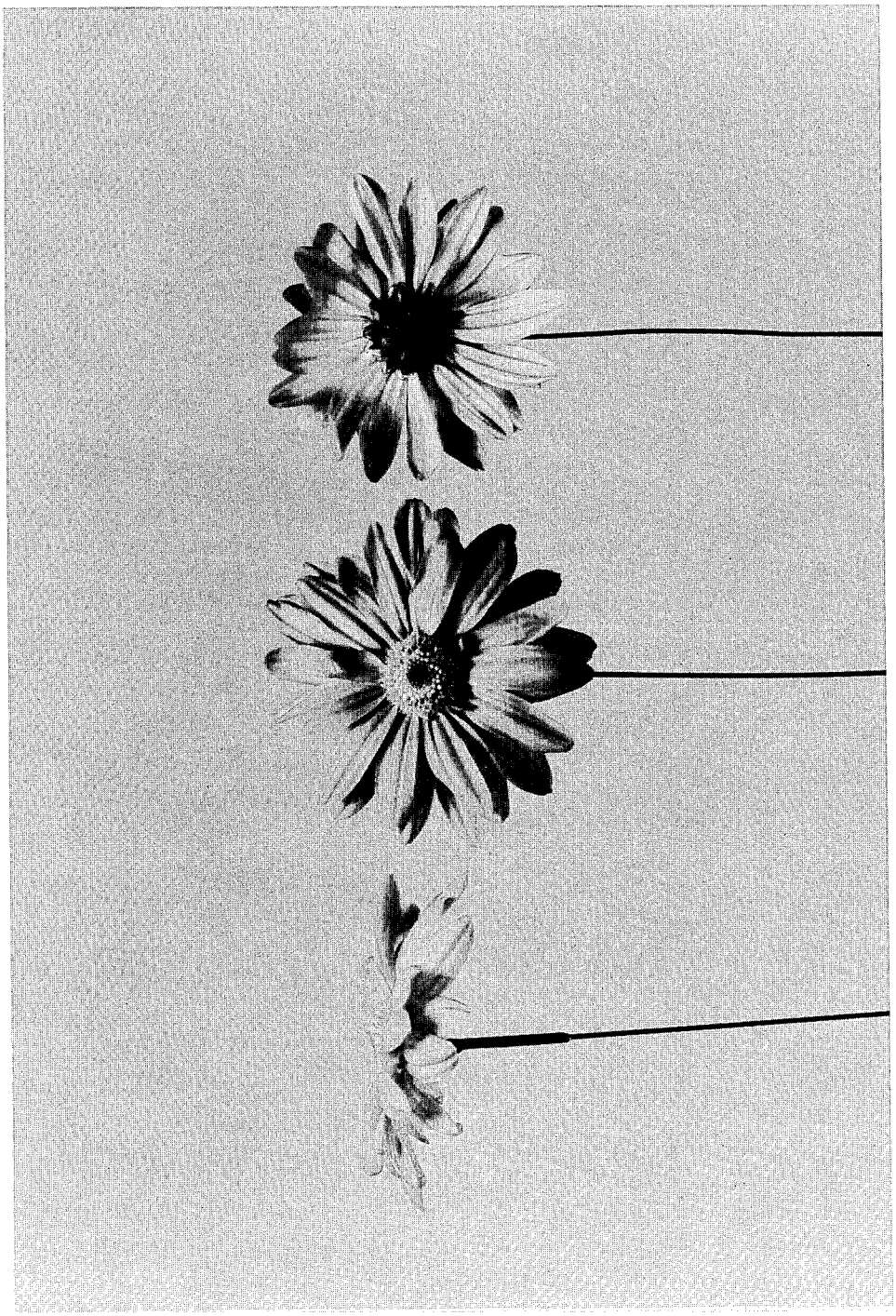

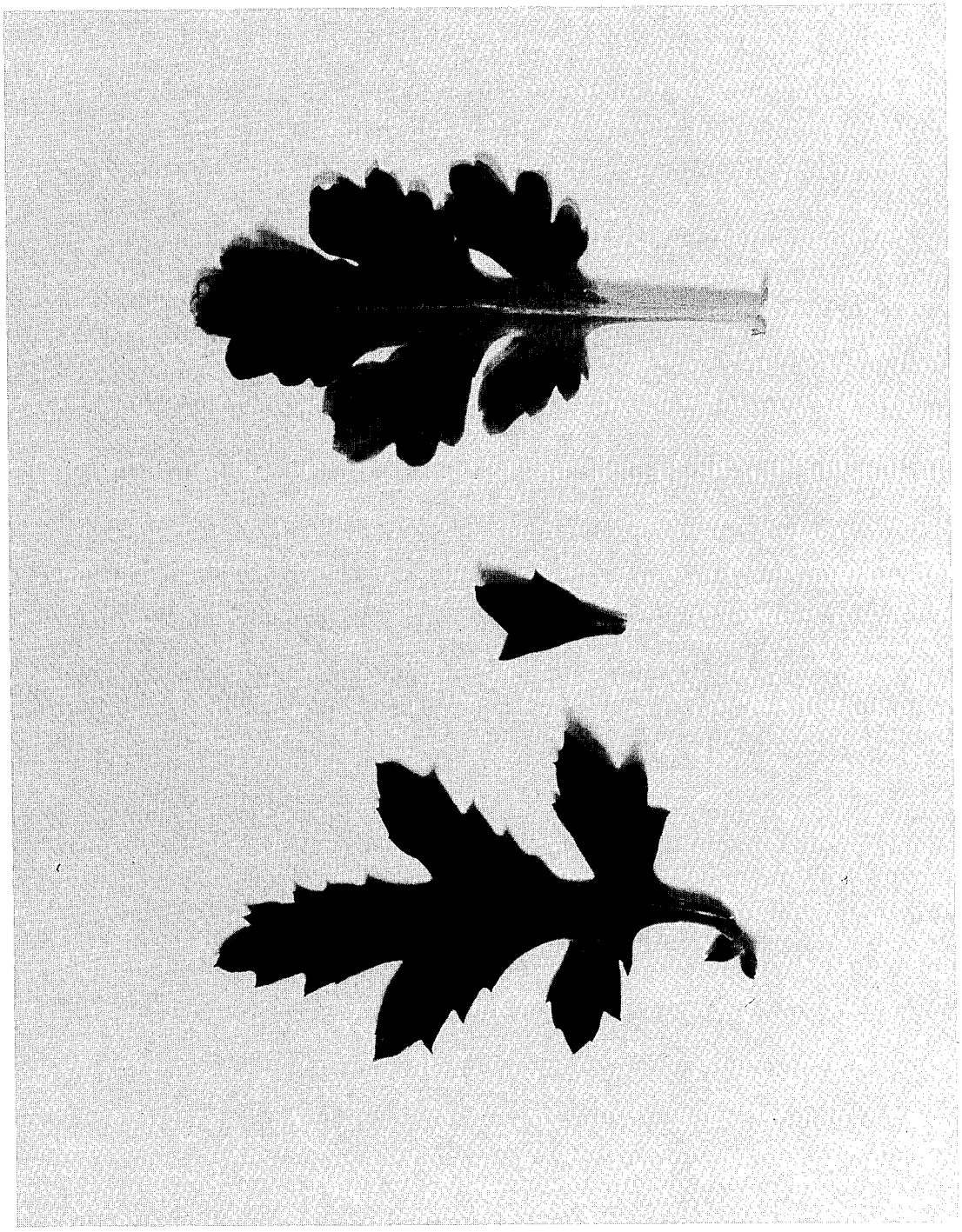

Plant Pat. 3,906

Patented June 15, 1976

3,906

CHRYSANTHEMUM PLANT

Walter H. Jessel, Jr., Doylestown, and William E. Duffett, Akron, Ohio, assignors to Yoder Brothers, Inc., Barberton, Ohio

Filed May 15, 1975, Ser. No. 577,891

Int. Cl. A01h *5/00*

U.S. Cl. Plt.—74 1 Claim

The present invention comprises a new and distinct cultivar of *Chrysanthemum morifolium,* Ramat., hereinafter referred to by the cultivar name Tantalizer (#72097002).

Tantalizer was originated from a cross made in a controlled breeding program in Barberton, Ohio in the year 1971. The female, or seed parent, was #68210008 (unnamed seedling), a bronze daisy originated by the present inventors from a cross between Dramatic (#67079001; U.S. Plant Pat. No. 3,189) and Aglow (#65781001; U.S. Plant Pat. No. 3,212). Both Dramatic and Aglow are products of the breeding program of the present inventors.

The male, or pollen parent of Tantalizer, was Nero (#21700E01; unpatented; commercially available), a red bronze daisy of parentage unknown to the present inventors.

Tantalizer was discovered and selected as a flowered seedling within the progeny of the stated cross by William E. Duffett and Walter H. Jessel, Jr. on Nov. 3, 1972 in a controlled environment in Barberton, Ohio.

Tantalizer is a product of a planned breeding program which had the objective of creating daisy type sprays adaptable to commercial cut programs with high gradeout (Society of American Florist standards), tall plant height, and efficient nine and ten week flowering response specifically for the fall, winter and spring flowering periods. These traits in combination were not present in previously available commercial cultivars.

The first act of asexual reproduction of Tantalizer was accomplished when vegetative cuttings were taken from the initial selection in Decmeber 1972 in a controlled environment in Barberton, Ohio by a technician working under formulations established and supervised by William E. Duffett and Walter H. Jessel, Jr. Horticultural examination of selected units initiated May 3, 1973 has demonstrated that the combination of characteristics as herein disclosed for Tantalizer are firmly fixed and are retained through successive generations of asexual reproduction.

Tantalizer has not been observed under all possible environments. The phenotype may vary significantly with variations in environment such as temperature, light intensity, and daylength. The following observations, measurements, and comparisons describe single stem spray plants grown in a greenhouse in Barberton, Ohio under environmental conditions which approximate those generally used in commercial practice, as described in Chart A and Chart B which appear at the end of the present specification.

The following traits have been repeatedly observed and are determined to be basic characteristics of Tantalizer which in combination distinguish this chrysanthemum as a new and distinct cultivar:

(1) Daisy inflorescence type with moderate longitudinal petal roll in opening stages.

(2) Flat inflorescence form not known to reflex.

(3) Diameter across face of inflorescence up to 4.0 inches at maturity.

(4) Orange bronze ray floret color with minimal color oxidation under fall, winter, and spring light conditions.

(5) Medium green disc floret color at immature, unopened stage.

(6) Minimal pollen development.

(7) Uniform nine week flowering response.

(8) Very tall plant height.

(9) Semi-upright branching habit.

(10) High percentage gradeout in top grades (SAF standards).

(11) Thin and weak peduncles during high light, high temperature periods (June through September).

The accompanying photographic drawings show typical inflorescence and foliage characteristics of Tantalizer with colors being as nearly true as possible with illustrations of this type. Sheet 1 is a color photograph of Tantalizer. Sheet 2 is a black and white photograph showing three views of the inflorescence of Tantalizer. Sheet 3 is a black and white photograph of the foliage of Tantalizer at three stages of growth.

Of the many commercial cultivars known to the present inventors, the most similar existing cultivars in comparison to Tantalizer are Crackerjack (#51026002; unpatented), Divinity (#57452002; unpatented), Galaxy (#46331007; unpatented), and Nero (#21700E01; unpatented). Reference is made to attached Chart C which compares certain characteristics of the above mentioned cultivars with the same characteristics of Tantalizer. General comparisons are as follows:

In comparison to Crackerjack, Tantalizer has a more orange ray floret color, green immature disc floret color, higher gradeout percentage in top grades (SAF standards), taller plant height, less abundant pollen, and shorter flowering response period. The inflorescence type of Tantalizer is similar to that of Crackerjack.

In comparison to Divinity, Tantalizer has orange bronze ray floret color, higher gradeout percentage in top grades (SAF standards), taller plant height, less abundant pollen, shorter flowering response period, and different inflorescence type. The immature disc florets of Tantalizer are similar in color to those of Divinity.

In comparison to Galaxy, Tantalizer has a more orange ray floret color, higher gradeout percentage in top grades (SAF standards), green immature disc floret color, taller plant height, less abundant pollen, and shorter flowering response period. The inflorescence type of Galaxy is similar to that of Tantalizer.

In comparison to Nero, Tantalizer has a more orange ray floret color, and taller plant height. The immature disc floret color, percentage gradeout in top grades (SAF standards), scarcity of pollen, flowering response period, and the inflorescence type of Tantalizer are similar to those of Nero.

In the following description, color references are made to The Munsell Limit Color Cascade, 1972 edition. The color values were determined between 2:00 and 2:30 p.m. on Mar. 11, 1975 under 160 foot candle light intensity and between 4:30 and 5:00 p.m. on June 27, 1975 under 160 foot candle light intensity at Barberton, Ohio.

BOTANICAL CLASSIFICATION

*Chrysanthemum morifolium*, Ramat., cv Tantalizer

(*I*) *Inflorescence*

(A) Capitulum:
*Form.*—Flat.
*Type.*—Daisy.
*Permanence.*—10–14 days.
*Diameter across face.*—3.0 to 4.0 inches.

(B) Corolla of ray florets:
*Texture (adaxial).*—Glabrous.
*Appearance and form.*—Ligulate.
*Arrangement.*—Whorled on receptacle.
*Persistence.*—Resists shatter.
*Color (abaxial).*—Approximately 29–11 (Mar. 11, 1975); to approximately 27–6 streaked with 29–11 (June 27, 1975).
*Color (adaxial).*—27–5 streaked with 29–10 to 29–11 (Mar. 11, 1975); 27–3 (June 27, 1975).

(C) Corolla of disc florets:
*Appearance.*—Gamepetalous, tubular; 5-lobed.
*Color.*—23–10 to 27–6.

(D) Reproductive organs:
*Androecium.*—Present disc florets only; syngenesious stamen; scant pollen.

*Gynoecium.*—Present both ray and disc florets; inferior, bicarpellate ovary; single style; 2-lobed stigma.

(*II*) *Plant*

(A) General appearance: Upright; very tall.
(B) Duration and texture: Herbaceous; perennial.
(C) Foliage:
*Color (abaxial).*—Approximately 21–15.
*Color (adaxial).*—Approximately 21–13 overlaid with white.
*Shape.*—Spatulate; deeply lobed.
*Texture.*—Glabrous.
*Arrangement.*—Alternate.
*Veination.*—Prominent.
*Margin.*—Coarsely serrated.

CHART A—AVERAGE GREENHOUSE CHRYSANTHEMUM ENVIRONMENTS USED FOR BARBERTON, OHIO

| Season | Temperature used (° F.) Night | Bright day | Cloudy day | Lighting used | Black cloth used | Supp., $CO_2$ |
|---|---|---|---|---|---|---|
| Fall | 65 to 56 | 65 to 80 | 60 to 75 | 2 to 4 weeks at 3 hours per night of 7–10 f.c. | To Sept. 15: on, 5:30 p.m., off, 7:30 a.m. | From Oct. 15: 300 p.p.m. |
| Winter | 58 to 62 | 65 to 70 | 60 to 65 | 2 to 5 weeks at 5 hours per night of 7–10 f.c. | None | 300 p.p.m. |
| Spring | 58 to 65 | 65 to 80 | 60 to 75 | 2 to 4 weeks at 5 hours per night of 7–10 f.c. | From Mar. 15: on, 5:30 p.m., off, 7:30 a.m. | To Apr. 15: 300 p.p.m. |
| Summer | 62 to 68 | 70 to 90 | 65 to 75 | 1 to 2 weeks at 3 hours per night of 7–10 f.c. | On, 6:00 p.m.; off, 8:00 a.m. | None. |

NOTE.—For intensity of direct solar radiation, refer to Chart B.

CHART B

INTENSITY OF DIRECT SOLAR RADIATION

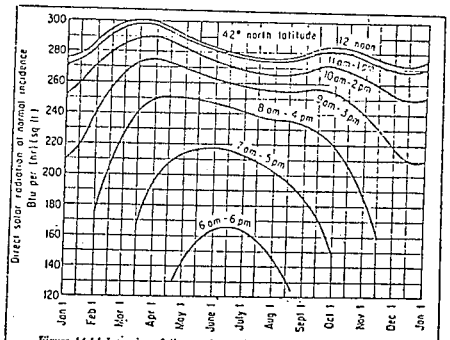

Figure 14.14 Intensity of direct solar radiation normal to the sun's rays at 42 degrees north latitude for an atmospheric clearness number of unity. (Reprinted by permission from *ASHAE Trans.*, Vol. 64, p. 64.)

CHART C—COMPARISON OF TANTALIZER WITH CRACKERJACK, DIVINITY, GALAXY AND NERO

| Cultivar | Ray floret color | Immature disc floret color | Gradeout (SAF) | Plant height | Pollen | Flowering response period (weeks) | Inflorescence type |
|---|---|---|---|---|---|---|---|
| Tantalizer | Orange bronze | Green | High | Very tall | Scant | 9 | Daisy. |
| Crackerjack | Red bronze | Yellow | Medium | Tall | Abundant | 12 | Do. |
| Divinity | White | Green | Low | do | Moderate | 10 | Anemone. |
| Galaxy | Copper bronze | Yellow | Medium | Medium | Abundant | 12 | Daisy. |
| Nero | Red bronze | Green | High | Tall | Scant | 9 | Do. |

NOTE.—Comparisons made of plants in a greenhouse in Barberton, Ohio under conditions as described in Chart A and Chart B.

We claim:

1. A new and distinct cultivar of chrysanthemum characterized particularly as to uniqueness by the combined characteristics of daisy inflorescence type with moderate longitudinal petal roll in opening stages, flat inflorescence form not known to reflex, diameter across face of inflorescence up to 4.0 inches at maturity, orange bronze ray floret color with minimal color oxidation under fall, winter, and spring light conditions, medium green disc floret color at immature, unopened stage, minimal pollen development, uniform nine week flowering response, very tall plant height, semi-upright branching habit, high percentage gradeout in top grades (SAF standards), and thin and weak peduncles during high light, high temperature periods (June through September).

No references cited.

ROBERT E. BAGWILL, Primary Examiner